(12) United States Patent
Malshe

(10) Patent No.: US 8,772,324 B2
(45) Date of Patent: Jul. 8, 2014

(54) COMPOSITION AND METHODS FOR THE TREATMENT OF WOUNDS

(76) Inventor: Keshav Malshe, Orlando, FL (US)

( * ) Notice: Subject to any disclaimer, the term of this patent is extended or adjusted under 35 U.S.C. 154(b) by 0 days.

(21) Appl. No.: 13/260,489

(22) PCT Filed: Mar. 18, 2010

(86) PCT No.: PCT/US2010/027778
§ 371 (c)(1),
(2), (4) Date: Jan. 9, 2012

(87) PCT Pub. No.: WO2010/111108
PCT Pub. Date: Sep. 30, 2010

(65) Prior Publication Data
US 2012/0095008 A1    Apr. 19, 2012

Related U.S. Application Data

(60) Provisional application No. 61/163,147, filed on Mar. 25, 2009.

(51) Int. Cl.
*A61K 31/4166* (2006.01)
*C07D 233/74* (2006.01)

(52) U.S. Cl.
USPC ........................................ 514/391; 548/321.1

(58) Field of Classification Search
CPC ......................... A61K 31/4166; A61K 31/375
USPC ......................... 514/342, 249, 391; 548/321.1
See application file for complete search history.

(56) References Cited

U.S. PATENT DOCUMENTS

| 5,602,183 A | 2/1997 | Martin et al. |
| 2011/0027366 A1* | 2/2011 | Kemp et al. ................... 424/484 |

FOREIGN PATENT DOCUMENTS

| CN | 1342491 A | * | 4/2002 |
| WO | WO 2006097701 A2 | * | 9/2006 |

OTHER PUBLICATIONS

Wynn et al., Wound care of a diabetic foot ulcer, International Journal of Pharmaceutical Compounding, Aug. 2004, vol. 8, No. 4, pp. 265-267.
Eddy et al., Topical Honey for Diabetic Foot Ulcer, Journal Fam Pract, Jun. 2005, vol. 54, No. 6, p-p 533-535.
El-Nahas et al., The Impact of Topical Phenytoin on Recalcitrant Neuropathic Diabetic Foot Ulceration, Journal Wound Care, Jan. 2009, vol. 18,No. 1, pp. 33-37.
Scheinfeld, N., Phenytoin in Cutaneous Medicine: Its uses, Mechanisms and Side Effects, Dermatology Online Journal, Aug. 2003, vol. 9, No. 3, p. 6.

* cited by examiner

*Primary Examiner* — Kendra D Carter
*Assistant Examiner* — Jason A Deck
(74) *Attorney, Agent, or Firm* — Timothy H. Van Dyke; Beusse, Wolter, Sanks, Mora & Maire, P.A.

(57) ABSTRACT

The present invention is directed to a wound composition comprising an effective amount of phenytoin and an effective amount of vitamin C. The present invention is further directed to a method of treating a wound in a patient comprising administering an effective amount of phenytoin and an effective amount of vitamin C to the wound.

7 Claims, 2 Drawing Sheets

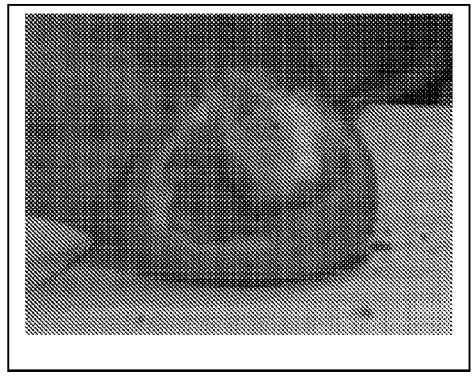
prior to treatment
FIG. 1
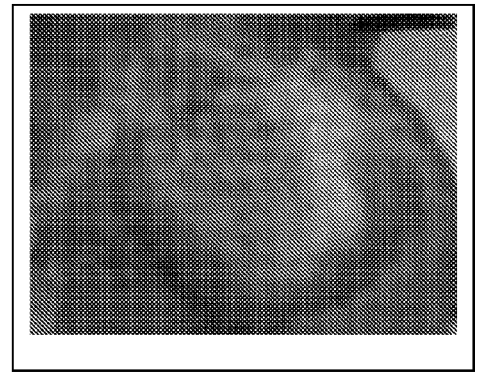
prior to treatment
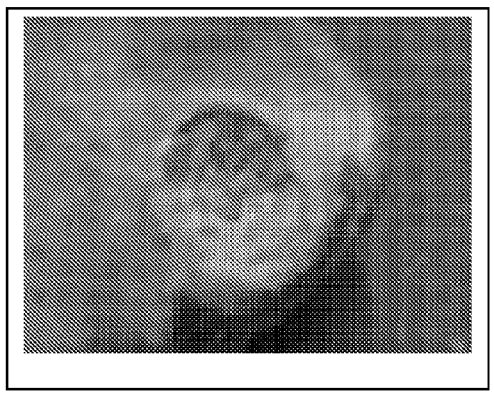
3 weeks of treatment
FIG. 2
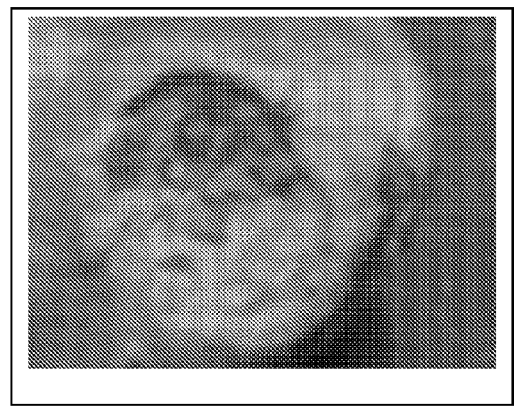
3 weeks of treatment

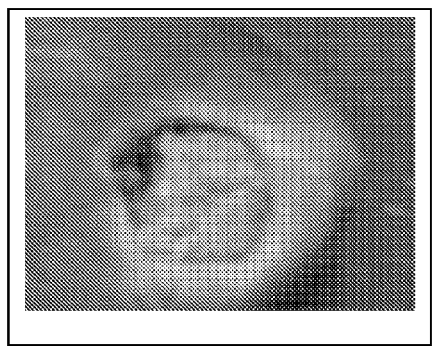
6 weeks of treatment
FIG. 3
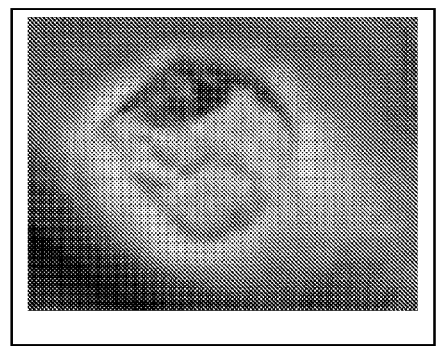
6 weeks of treatment
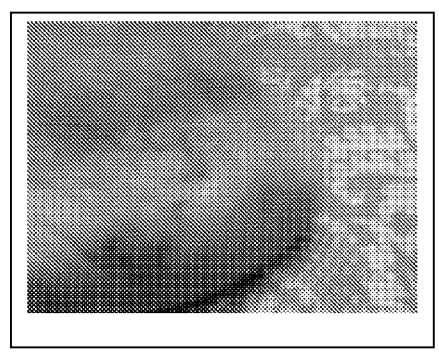
18 weeks of treatment
FIG. 4
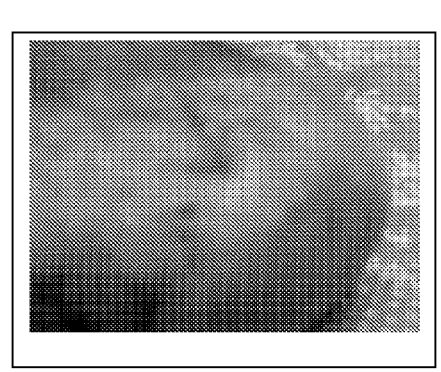
18 weeks of treatment

COMPOSITION AND METHODS FOR THE TREATMENT OF WOUNDS

RELATED APPLICATIONS

This application claims priority to U.S. Ser. No. 61/163,147 filed Mar. 25, 2009, which is incorporated herein in its entirety.

FIELD OF THE INVENTION

The present invention relates to compositions comprising a mixture of phenytoin with vitamin C and/or other conjunctive compounds, for use in the treatment of wounds, e.g., diabetic ulcers, and to methods for treating such wounds with the compositions.

BACKGROUND OF THE INVENTION

Generally, when the skin of an individual is torn, cut or punctured (wounded), the body naturally reacts to regenerate dermal and epidermal tissue to close the wound. The wound regeneration process typically includes a set of complex biochemical events that take place in a closely orchestrated cascade to repair the damage. These events overlap in time, but may be categorized into different phases, namely the inflammatory, proliferative, and remodeling phases.

In the inflammatory phase, bacteria and debris are phagocytized and removed, and factors are released that cause the migration and division of cells involved in the proliferative phase. In the proliferative phase, the principal steps include angiogenesis, fibroplasias, granulation tissue formation, epithelialization, and wound contraction. Angiogenesis involves the development of new capillary blood vessels for the wound area to provide oxygen and nutrients to the healing tissue. In fibroplasia and granulation tissue formation, fibroblasts grow and form a new, provisional extracellular matrix (ECM) by excreting collagen and fibronectin. In epithelialization, epithelial cells crawl across the wound bed to cover the bed. In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

It is known that a number of disease states hinder the normal wound healing process. For example, individuals with diabetes often experience problems with what are termed "diabetic foot ulcers." Diabetic foot ulcers are sores or wounds, typically, on the feet that typically occur in individuals having diabetes. Oftentimes, these diabetic ulcers occur as a direct or indirect result of nerve damage in the feet of the individual as the prolonged high blood sugar levels associated with diabetes is linked with damage to the nerves in the feet. Such nerve damage in the feet, referred to as peripheral neuropathy, can cause loss of sensation as well as cause deformities of the feet. Due to the loss of sensation, individuals with peripheral neuropathy may hurt their feet by repetitive minor trauma (e.g., by prolonged walking) or a single major trauma (e.g., by scraping skin, stepping on objects, immersing feet in hot water, cutting toenails inappropriately, or wearing ill-fitting shoes), but nevertheless may not notice such injuries. A further complication of diabetes is a reduction in blood flow to the feet due to the arterial blockage or other causes, thereby severely inhibiting the body's ability to adequately provide complete the proliferative stage of wound regeneration/healing described above. As a result, once the skin of the foot is torn, cut, or punctured, the wound healing process (e.g., the proliferative phase) may be inordinately slow in repairing the wound. Further, once a serious wound develops, the risk of infection is high as the individual's body is simply unable to heal the wound. Even further, once an infection starts, the infection may be very difficult to reverse, and amputation of the affected limb is common.

A number of treatments have been proposed to speed wound healing in patients having diabetic ulcers. These treatments include the use of skin grafts or "tissue equivalents." Tissue equivalents involve the isolation of replacement skin cells that are expanded and seeded onto or into a supporting structure, such as a three-dimensional bio-resorbable matrix, or within a gel-based scaffold. Both skin grafts and tissue equivalents are notably complex and, especially in the case of reduced blood flow to the patient's legs or feet, are often unsuccessful. Other treatments involve the direct application or injection at the wound site of particular pharmaceutical agent(s). Phenytoin, for example, is a drug that has been used for decades in the treatment of convulsive disorders. Recently, however, phenytoin has been investigated for its wound healing properties in the treatment of diabetic ulcers. See Bhatia, A., Prakash, S., Topical Phenytoin for Wound Healing. Dermatology Online Journal 2004; 10(1):5; and Mutyhukumarasamy M G, Sivakumar G, Manoharan G. Topical phenytoin in diabetic foot ulcers. Diabetes Care 1991; 14:909-11. Mutyhukumarasamy et al. allegedly found an improvement in the mean healing time for patients with diabetic ulcers in patients treated with phenytoin (21 days) vs. a control group (45 days). Nevertheless, the use of phenytoin for the control and healing of wounds, including diabetic ulcers, has not become a standard treatment, primarily because the incidence of amputation remains high and the degree of wound healing remains insufficient. Accordingly, there remains a need for an improved composition and method of treatment for diabetic ulcers.

BRIEF DESCRIPTION OF THE DRAWINGS

FIG. 1 depicts an untreated diabetic ulcer of a male patient on a bottom portion of a foot of the patient; and FIG. 2 depicts the diabetic ulcer of FIG. 1 after three weeks of treatment with a wound composition in accordance with the present invention.

FIG. 3 depicts the diabetic ulcer of FIG. 1 after six weeks of treatment.

FIG. 4 depicts the diabetic ulcer of FIG. 1 after eighteen weeks of treatment.

DETAILED DESCRIPTION OF THE INVENTION

The present inventors have surprisingly found that the combination of phenytoin and vitamin C provides improved wound healing properties to a patient over the use of either phenytoin or vitamin C alone. Thus, the present invention provides a potent wound healing and potentially limb-saving composition utilizing readily available pharmaceutical products.

In accordance with one aspect of the present invention, there is provided a wound composition comprising an effective amount of phenytoin and an effective amount of vitamin C. The phenytoin and vitamin C may be provided as a single composition or may be applied independent of one another.

In accordance with another aspect of the present invention, there is provided a pharmaceutical composition comprising an effective amount of phenytoin and an effective amount of vitamin C and at least one pharmaceutical acceptable excipient.

In accordance with yet another aspect of the present invention, there is provided an article of manufacture comprising packaging material, an effective amount of phenytoin, and an effective amount vitamin C, wherein the packaging material comprises a label or package insert indicating that the effective amount of phenytoin and the effective amount of vitamin C can be administered to a patient for accelerating a healing process of a wound.

In accordance with yet another aspect of the present invention, there is provided a method of treating a wound in a patient comprising administering topically an effective amount of phenytoin and an effective amount of vitamin C to the wound.

In accordance with yet another aspect of the present invention, there is provided a method of treating a wound in a patient comprising administering parenterally an effective amount of phenytoin and an effective amount of vitamin C to the wound.

In accordance with yet another aspect of the present invention, there is provided a method of accelerating the healing of a wound in a patient comprising administering an effective amount of phenytoin and an effective amount of vitamin C to the wound.

In accordance with yet another aspect of the present invention, there is provided a method for treating a diabetic ulcer comprising administering to a patient in need thereof a wound composition comprising an effective amount of phenytoin and an effective amount of vitamin C.

DEFINITIONS

As used herein, the use of the word "a" or "an" when used in conjunction with the term "comprising" in the claims and/or the specification may mean "one," but it is also consistent with the meaning of "one or more," "at least one," and "one or more than one."

The term "wound" as used herein refers to any break in the epithelium resulting from a cut, abrasion, adhesion, surgical incision, thermal, chemical, or friction burn, ulcer, or the like, as a result of an accident, incident, surgical procedure, or the like. Wound can be further defined as acute and/or chronic. Compositions of the present invention have been found to be particularly useful in the treatment of diabetic ulcers, which are a type of wound as defined herein.

The term "pharmaceutically acceptable carrier" as used herein includes any and all solvents, dispersion media, coatings, antibacterial and antifungal agents, isotonic and absorption delaying agents, and the like. The use of such media and agents for pharmaceutically active substances is well known in the art.

The term "pharmaceutical composition" as used herein refers to a wound composition as described herein that this dispersed in a pharmaceutically acceptable carrier.

The term "patient" as used herein refers to any mammalian patient to which a wound composition is administered according to the methods described herein. In a specific embodiment, the compositions and methods of the present invention are employed to treat a human patient.

The term "effective amount" as used herein refers to an amount effective, at dosages and for periods of time necessary to achieve a desired result. The desired result may be an improvement in the wound healing process (e.g., by reducing a surface area of the wound), remediation of the symptoms of the wound (e.g., pain, infection, and the like), shortening of the duration of any stage in the wound healing process, stabilization of the state of wound (e.g., infection), prevention or slowing of the development of wound progression, prevention of, delay or slowing of wound progression, delay or slowing of wound onset, amelioration or palliation of the wound state, and remission (whether partial or total), whether detectable or undetectable.

The term "topical administration" as used herein includes the contact of the wound compositions of the present invention with tissue on or about the wound area.

The term "parenteral administration" as used herein includes any form of administration in which a composition is delivered or absorbed into the patient without involving absorption via the intestines. Exemplary parenteral administrations that are used in the present invention include, but are not limited to intradermal or subcutaneous administration.

The term "treating" and "treatment" as used herein refers to an approach for obtaining beneficial or desired results, including clinical results. Beneficial or desired clinical results can include, but are not limited to, an improvement in the wound healing process (e.g., by reducing a surface area of the wound), remediation of the symptoms of the wound (e.g., pain, infection, and the like), shortening of the duration of any stage in the wound healing process or the overall wound healing process, stabilization of infection (if any), and remission (whether partial or total), whether detectable or undetectable.

As used herein, the term "phenytoin" includes phenytoin, any pharmaceutically acceptable salt thereof, and/or any derivative thereof. Phenytoin was first synthesized by German chemist Heinrich Biltz in 1908. Phenytoin has the chemical structure, $C_{15}H_{12}N_2O_2$, and is also known as diphenylhydantoin or 5,5-diphenyl-2,4-imidazolidinedione. Phenytoin is commercially available worldwide as phenytoin or in the form of a pharmaceutically acceptable salt, e.g., phenytoin sodium, under the names Phenytek®, Dilantin®, Dilantin® Kapseals®, Dilantin® Infatabs®, Epotoin, Diphenin, Difnenin, Dipheninum, and/or Phydum™, for example. Exemplary phenytoin derivatives are set forth in U.S. Pat. No. 5,306,617 and in EP 0471338 B1, the entirety of each of which are hereby incorporated by reference.

As used herein, "Vitamin C" refers to ascorbic acid, the reduced form of ascorbic acid (ascorbate), mineral ascorbates (such as sodium, potassium, calcium, zinc, molybdenum, chromium and manganese ascorbates), ascorbyl palmitate, D-isoascorbic acid, and any isomers and/or esters of any of the aforementioned compounds. U.S. Pat. Nos. 5,801,192 and 6,744,114 are cited to and incorporated herein in its entirety for teaching on vitamin C derivatives and analogues that may be used as the vitamin C component. While not wishing to be bound by theory, it is believed that Vitamin C is therapeutically effective for the production and maintenance of collagen, as well as for the metabolism of folic acid, tyrosine and tryptophan. Vitamin C is also believed to enhance the body's immune response, thereby protecting against infection, and aiding in the production of thyroxine. Of importance, Vitamin C also is further believed to have antioxidant properties. Vitamin C may be derived from any natural source, such as Vitamin C extracted from rose hips, acerola cherries, peppers, citrus fruits, corm syrup, or sago palm, or may be produced synthetically. Vitamin C is also readily commercially available from numerous commercial sources. When added to the wound compositions of the present invention, Vitamin C synergistically improves the therapeutic effectiveness of the phenytoin.

While not wishing to be bound by theory, it is believed that when applied to a wound, such as a diabetic ulcer, the phenytoin of the wound compositions of the present invention may assist wound healing by one or more of processes, such as by stimulating fibroblast proliferation, enhancing the formation of granulation tissue, decreasing collagenase activity, promoting deposition of collagen and other connective components, decreasing bacterial contamination, and decreasing wound exudate. See Bhatia, A., Prakash, S., Topical Phenytoin for Wound Healing. Dermatology Online Journal 2004; 10(1):5. Mutyhukumarasamy M G, Sivakumar G, Manoharan G. Topical phenytoin in diabetic foot ulcers. Diabetes Care 1991; 14:909-11.

The present inventors have surprisingly found, however, that when an amount of Vitamin C is added to a wound composition comprising phenytoin, the therapeutic effectiveness of the wound composition in treating wounds, e.g., diabetic ulcers, is markedly enhanced relative to phenytoin or vitamin C alone, and other compositions. Diabetic ulcers are notoriously difficult to control and treat due to decreased blood flow to the affected area, associated nerve and tissue damage (if present), age, condition of the patient, and other factors. Often, when the wound will not properly heal and infection reaches an unacceptable or dangerous state, the limb of the individual is amputated above the wound site. The wound compositions of the present have proven to be effective in promoting wound healing and reducing the likelihood of amputation of the affected limb.

In an embodiment, the wound compositions of the present invention may also comprise an additional component, or component that substitutes for vitamin C, that acts as an antioxidant and/or further aids in promoting or improving wound healing relative to a composition without the additional component. For example, in one embodiment, the wound composition may further comprise an effective amount of vitamin E. By "Vitamin E," it is meant any one or combination of the eight forms of Vitamin E comprising the four tocopherols and the four tocotrienols, including any succinate, nicotinate and acetate salts derivatives thereof. Each of these forms of Vitamin E has a "d" form, which is the natural form, and a "dl" form, which is the synthetic form. In one embodiment, the composition of the present invention comprises d-α tocopherol, or a salt derivative thereof, as this is the most active form of Vitamin E. Alternatively, in another embodiment, an effective amount of Vitamin E is utilized in the wound composition in place of the vitamin C. Vitamin E is believed to have anti-inflammatory effect when applied topically, as well as antioxidant properties. Vitamin E may be extracted from such natural products, such as vegetable oils (olive, sunflower, and safflower oils), nuts, whole grains, and green leafy vegetables. Alternatively, Vitamin E is also readily commercially available from numerous commercial sources. In another embodiment, the composition includes foliate, or follic acid, and/or magnesium, in combination with phenytoin, with or without vitamin C and/or vitamin E.

The wound compositions of the present invention may be provided in any suitable form for administration to a wound of a patient. For example, the wound compositions of the present invention may be provided and/or manufactured in a formulation for topical administration and/or parenteral administration, such as a topical formulation, an injectable formulation, and/or any other suitable formulation. It is understood that the active ingredients may be provided individually (with or without instructions for future mixing) or together (mixed, non-mixed, or with instructions for future mixing) in the respective formulation. Further, the wound composition may be prepared by known methods for the preparation of pharmaceutically acceptable compositions suitable for administration to a patient, such that an effective quantity of the active ingredients is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

In one embodiment, the wound composition is provided in the form of a topical composition, such as a powder, ointment, lotion, cream, and/or gel. In a particular embodiment, the topical composition may be provided in the form of a powder. In another embodiment, the active compounds of the composition are mixed in a composition that utilizes honey as a carrier. The topical composition may comprise phenytoin in an amount from about 100 g to 1000 g, and in a particular embodiment about 300 g. Similarly, the topical composition may comprise Vitamin C in an amount of about 100 g to 1000 g, and in a particular embodiment about 500 g. The ratio of phenytoin to vitamin C may be from about 1:10 to 1:1 by weight. In a particular embodiment, the ratio of phenytoin to vitamin C may be from about 1:5 to about 1:1 by weight, e.g. 300 mg phenytoin to 500 mg vitamin C.

When a wound composition of the present invention is provided in the form of a topical composition, e.g., powder, ointment, lotion, cream, and/or gel, the wound composition may further include other cosmetic ingredients and pharmaceutically acceptable topical carriers which have substantially non-irritating, skin compatible components. Such suitable cosmetic and pharmaceutical agents include, but are not limited to, moisturizers, stabilizers, preservatives, antiseptics, lubricants, humectants, gelling agents, chelating agents, skin penetration enhancers, emollients, colorants, solvents, fatty bodies, thickening agents, emulsifiers, and/or any other excipient, which does not alter the therapeutic effect of the active ingredients, e.g., phenytoin and vitamin C.

When any one of the wound compositions described herein is provided in the form of an injectable solution, the injectable solution may comprise phenytoin in an amount from about 200 g to 400 g, and in a particular embodiment, about 300 mg. In addition, the injectable solution may comprise Vitamin C in an amount from about 100 g to 1000 g, and in particular embodiment, about 500 g. The ratio of phenytoin to vitamin C may be from about 1:10 to 1:1 by weight. In a particular embodiment, the ratio of phenytoin to vitamin C may be from about 1:5 to about 1:1 by weight, e.g. 300 mg phenytoin to 500 mg vitamin C. Optionally, the phenytoin and the vitamin C may be mixed with a suitable of 10 N saline to form the injectable solution.

In addition, when provided in the form of in injectable solution, the injectable solution may further include any suitable pharmaceutically acceptable additives. Suitable pharmaceutically acceptable additives include additives employed customarily in a injection formulation, such as a stabilizer (ascorbic acid, sodium pyrosulfite and the like), a surfactant (polysorbate 80, macrogol and the like), a solubilizing agent (glycerin, ethanol and the like), a buffering agent (phosphoric acid and its alkali metal salt, citric acid and its alkali metal salt and the like), an isotonizing agent (sodium chloride, potassium chloride and the like), a dispersing agent (hydroxypropylmethyl cellulose, dextrin), a pH modifier (hydrochloric acid, sodium hydroxide and the like), a preservative (ethyl p-oxybenzoate, benzoic acid and the like), a solubilizer (concentrated glycerin, meglumine and the like), a solubilizing aid (propylene glycol, sugar and the like), and/or a painkiller (glucose, benzyl alcohol and the like) as desired. Any of these agents or additives may be added in an amount employed customarily in a formulation for injection, and preferably do not alter the therapeutic effect of the active ingredients of the present invention, e.g., phenytoin and vitamin C.

In an embodiment, the present invention also provides an article of manufacture comprising packaging material and an effective amount of phenytoin and vitamin C for the treatment of a wound, e.g., a diabetic ulcer. The packaging material may comprise a label or package insert indicating that the effective amount of phenytoin and the effective amount of vitamin C can be administered to a patient, e.g. a human patient, for inducing or accelerating healing of the wound. The label or package insert may comprise user-readable and/or computer-readable information embodied on any suitable medium, such as a paper insert or a computer-readable disc.

When a wound composition as described herein is a topical formulation, the wound composition may be applied directly to the wound in an amount effective to substantially cover the wound with the wound composition. Also, when the wound composition is a topical composition, e.g., cream, ointment, or the like, it is generally desirable to apply the wound composition directly to the wound by any suitable sterile applicator or sterile method of application known in the art.

In addition, when a wound composition as described herein is provided as an injectable solution, the injectable solution may be injected directly into the wound of the patient, such as by intradermal or subcutaneous injection, or otherwise injected into an about the wound area of the patient using a sterile syringe or other suitable device.

When applying and/or injecting the wound composition onto and/or to the wound, it may be desirable to administer a suitable analgesic by any suitable method known in the art beforehand, e.g., benzyl alcohol, chlorobutanol, to reduce pain and/or further inflammation in the wound area.

One skilled in the art would readily appreciate that the administration duration and dosage of the wound composition may be determined or adjusted based on the age, body weight, general condition, sex, diet, the severity of the wound, and/or degree of inflammation and/or infection associated with the wound. Effective amounts of the wound composition can be given repeatedly, depending upon the effect of the initial treatment regimen. Administrations are typically given periodically, while monitoring any response. It will be recognized by a skilled person that lower or higher dosages or number of applications other than those indicated herein may be given, according to the administration schedules and routes selected.

In an embodiment, the present inventors have found the wound compositions of the present invention are particularly effective when administered at least once daily for a first week's time. Thereafter, the wound compositions may be applied to the wound at least once a week until such time as the wound is satisfactorily healed. In one embodiment, a wound composition is applied once a week (after the initial daily application) for a period of at least seven weeks. It is understood that prior to each application, the wound may be rinsed with a sterile solution, such as saline, and allowed to dry. Thereafter, a wound composition may be applied and the wound wrapped in a suitable dressing.

An exemplary fresh diabetic ulcer of an exemplary patient is shown in FIG. 1. Upon treatment with a wound composition of the present invention, new signs of skin formation are likely to be present within three weeks (wound healing by secondary intention), particularly if the composition if applied to the wound daily for at least the first 7-10 days. Within weeks (after the daily application), it is expected that the wound will begin to appear generally healthier, that granulation tissue will be deposited, and that wound will begin to close as is generally shown in FIG. 2. After 10-18 weeks of weekly treatment, it is expected that the wound will be 90-100% closed and healed, see FIGS. 3-4.

It is further understood that the wound compositions of the present invention as described herein may be employed alone in the treatment, or may be combined with a concomitant drug, which is administered to the patient independently of the wound composition or as part of the same formulation. Such concomitant drugs may be delivered simultaneously, before and/or after the administration of the wound composition. Suitable concomitant drugs may include, by way of example only, vasodilators, vasoconstrictors, hypertensive agents, antibacterial agents, antibiotics, antifungal agents, non-steroidal antiinflammatory agents, steroidal agents, anesthetics, and/or diabetes agents.

Suitable vasodilators include, but are not limited to, manidipine, nicardipine, nilvadipine, nisoldipine, nitrendipine, benidipine, amlodipine, aranidipine, budralazine, cadralazine, ecarazine, hydralazine, todralazine, oxyphedrine, diltiazem, tolazoline, hexobendine, bamethan, clonidine, methyldopa, guanabenz, and the like.

Suitable vasoconstrictors include, but are not limited to, dopamine, dobutamine denopamine and the like.

Suitable hypertensive agents include, but are not limited to, dopamine, dobutamine, denopamine, digitoxin, digoxin, methyldigoxin, lanatoside C, G-strophantin, and the like.

Suitable antibacterial agents include, but are not limited to, sufonamides, such as sulfamethizole, sulfisoxazole, sulfamonomethoxin, sulfamethizole, salazosulfapyridine, silver sulfadiazine, and the like, and quinolones, such as nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin, and the like.

Suitable antibiotics include, but are not limited to, tetracyclin hydrochloride, ampicillin, piperacillin, gentamycin, dibekacin, kanendomycin, lividomycin, tobramycin, amikacin, fradiomycin, sisomicin, tetracyclin, oxytetracyclin, rolitetracyclin, doxycyclin, ampicillin, piperacillin, ticarcillin, cefalotin, cefapirin, cefaloridine, cefaclor, cefalexin, cefroxadine, cefadroxil, cefamandole, cefotoam, cefroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazon, ceftizoxime, moxalactam, thienamycin, sulfazecin, azthreonam and their salts, griseofulvin, lankacidin [J. Antibiotics, 38, 877-885 (1985)], and the like.

Suitable antifungal agents include, but are not limited to, polyene-based antibiotics (e.g., amphotericin B, nystatin, trichomycin); griseofulvin, pyrrolnitrin, and the like; cytosine metabilism antagonists (e.g., flucytosine); imidazole derivatives (e.g., econazole, clotrimazole, miconazole nitrate, bifonazole, croconazole); triazole derivatives (e.g., fluconazole, itraconazole, azole-based compounds, e.g., [2-[(1R, 2R)-2-(2,4-difluorophenyl)-2-hydroxy-1-methyl-3-(1H-1,2, 4-triazol-1-yl)propyl]-4-[4-(2,2,3,3-tetrafluoropropoxy) phenyl-3-(2H,4H)-1,2,4-triazolone); thiocarbamic acid derivatives (e.g., trinaphthol); echinocandin-based derivatives (e.g., caspofamgine, FK-463, V-Echinocadin), and the like.

Suitable non-steroidal antiinflammatory agents include, but are not limited to, acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesilate, camostat mesilate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone, and their salts.

Suitable steroidal agents include, but are not limited to, dexamethasone, hexestrol, methimazole, betamethasone, triamcinolone, triamcinolone acetonide, fluorocinonide, fluorocinolone acetonide, prednisolone, methylprednisolone, cortisone acetate, hydrocortisone, fluorometholone, beclometasone dipropionate, estriol, and the like.

Suitable anesthetics include, but are not limited to, cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine, and the like, or other systemic, inhalation, or intravenous anesthetics.

Suitable diabetes agents include, but are not limited to, actos, lodiglitazon, kinedak, penfill, humalin, euglucon, glimicron, daonil, novolin, monotard, insulins, glucobay, dimelin, rastinon, bacilcon, deamelin S, Iszilins]; hypothyroidism treating agent [dried thyroid gland (thyreoid), levothyroxine sodium (thyradin S), liothyronidin sodium (thyronine, thyromin), and the like.

The ratio between a compound of the present invention and a concomitant drug in a concomitant formulation may be selected appropriately on the basis of the target, route, and disease/condition of the patient and may be readily determined by one skilled in the art. In a particular embodiment, the present invention includes a method of treating a wound comprising administering to a patient in need thereof a wound composition comprising an effective amount of phenytoin and an effective amount of vitamin C along with an effective amount of an antibiotic to aid in combating wound infection.

The following examples are not understood to be limiting, but are useful in illustrating the effectiveness of a wound composition comprising phenytoin and vitamin C over a wound composition having phenytoin alone as an active ingredient.

Example 1

A 38-year old female was presented for a laceration, located on the dorsum of the left foot. Of note, the patient had already undergone an amputation of a portion of the right leg for a non-healing diabetic ulcer. The patient had developed the present wound over at least the previous 2 weeks. Previously also, the patient had been seen by a general surgeon for the present wound and was advised to have an amputation of the left leg (below knee amputation). A review of the patient's medical history and an examination of the patient found that the patient: (1) had been diagnosed with insulin-dependent diabetes mellitus 15 years previously and had been living with the condition since; (2) had no known drug allergies; (3) undergoes a daily regimen of 50 IU (70/30 Insulin-Novoline) in the A.M. and 25 IU (70/30 insulin) in the P.M.; (4) does not personally smoke or abuse alcohol; (5) (upon examination) had no other abnormalities in other systems, including the cardiovascular and respiratory systems; (6) (upon examination) had intact vital signs (Temp: 99.5° F., Pulse: 110/min; Blood Pressure: 110/70 mmHg; Respiration Rate: 20/min.); and (7) (upon examination) had a blood sugar of about 160 mg.

Examination of the patient's left foot showed that the wound appeared to be infected. A greenish discharge was also noted at the wound site. The area around the wound was erythematous and there was noted tenderness on palpation. The size of the wound was recorded to be approximately 5 cm×2 cm×3 cm. A wound swab also indicated the presence of *staphylococcus aureus*-methicillin sensitive. A treatment plan was established for the patient. Under the treatment plan, the patient received: 1) Insulin 70/30 (Novoline) 50 IU morning, 25 IU night; and 2) intravenously, Co-Amoxiclav 1.2 g+Gentamicin 80 mg+Metronidazole 400 mg in 100 ml N Saline/30 min (every 8 hours). After the injection of the intravenous antibiotics, the patient began taking oral antibiotics: 1) Co-Amoxiclav 625 mg (2 tablets) (twice daily); 2) Ciprofloxacin 500 mg once daily for 2 weeks; and 3) Ibuprofen 600 mg for 5 days (every 8 hours). Thereafter, the wound was cleaned with saline solution. A wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after the 9 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue had formed. At week 9, approximately 80% of the wound had healed. At week 10, approximately 90% of the wound had healed. At week 11, the wound had completely healed and the recommendation of amputation was not carried out.

Example 2

A 59 year-old female patient was presented for a laceration, located on the heal of the right foot. Of note, the patient had developed the present wound over at least the previous week. Previously also, the patient had been seen by a general surgeon for the present wound and was advised to have an amputation of the right leg (below knee amputation). A review of the patient's medical history and an examination of the patient found that the patient: (1) had been diagnosed with diabetes mellitus 10 years previously and had been living with the condition since; (2) had no known drug allergies; (3) undergoes a daily regimen of 30 IU (70/30 Insulin-Novoline) in the A.M. and 10 IU (70/30 insulin) in the P.M.; (4) does not personally smoke or abuse alcohol; (5) (upon examination) had no other abnormalities in other systems, including the cardiovascular and respiratory systems; (6) had intact vital signs (Temp: 99.5° F.; Pulse: 110/min; Blood Pressure: 110/70 mmHg; Respiratory Rate: 20/min.); and (7) (upon examination) had a blood sugar of about 160 mg.

Examination of the patient's left foot showed that the wound appeared to be infected. A greenish discharge was also noted at the wound site. The area around the wound was erythematous and there was noted tenderness on palpation. The size of the wound was recorded to be approximately 5 cm×2 cm×3 cm. A wound swab also indicated the presence of *staphylococcus aureus*-methicillin sensitive. A treatment plan was established for the patient. Under the treatment plan, the patient received: 1) 70/30 (Insulin-Novoline) 30 IU in the A.M., 10 IU in the P.M.; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) (twice daily); 2)

Ciprofloxacin 500 mg once daily for 2 weeks; and 3) Ibuprofen 600 mg every 8 hours for 5 days. Thereafter, the wound was cleaned with saline solution. A wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 5 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 50%) had formed. At week 9, approximately 80% of the wound had healed. At week 10, approximately 90% of the wound had healed. At week 11, the wound had completely healed and the recommendation of amputation was not carried out.

Example 3

A 62-year old male patient was presented for a post-amputation, non-healing wound on the right leg that had been developing over the previous week. Of note, the patient had already undergone an amputation of the right toe for another non-healing diabetic ulcer. A review of the patient's medical history and an examination of the patient found that the patient: (1) had been diagnosed with diabetes mellitus 22 years previously and had been living with the condition since; (2) had no known drug allergies; (3) undergoes a daily regimen of 30 IU (70/30 Insulin-Novoline) in the A.M. and 10 IU (70/30 insulin) in the P.M.; (4) does not personally smoke or abuse alcohol; (5) (upon examination) had no other abnormalities in other systems, including the cardiovascular and respiratory systems; (6) (upon examination) had intact vital signs (Temp: 97.2 F; Pulse: 75/min; Blood Pressure: 110/70 mmHg; Respiratory Rate: 20/min.); and (7) (upon examination) had a blood sugar of about 160 mg.

Examination of the patient's right lower leg showed that the wound appeared to be infected. A greenish discharge was also noted at the wound site. The area around the wound was erythematous and there was noted tenderness on palpation. The size of the wound was recorded to be approximately 12 cm×5 cm×2 cm. From the previous amputation, stitches had broken in 3 places. A wound swab also indicated the presence of *staphylococcus aureus*-methicillin resistant. A treatment plan was established for the patient. Under the treatment plan, the patient received: 1) Insulin 70/30 (Novolin) 50 IU morning, 25 IU night; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) (twice daily); 2) Ciprofloxacin 500 mg once daily for 2 weeks; and 3) Ibuprofen 600 mg for 5 days (every 8 hours). Thereafter, the wound was cleaned with saline solution. The patient was also started on Insulin R 25 IU 3 times daily to control blood sugar so as to not inhibit wound healing. A wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next 9 days. Thereafter, the patient began weekly visits. With each visit, the wound was cleaned with saline solution and the powdered wound composition was applied topically to the wound, and redressed. In each visit, the wounds were noted to be generally healthy. At week 1 (after the 5 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 10, the wound had healed completely and the recommendation of amputation was not carried out.

Example 4

A 50-year old male patient was presented for a post-amputation, non-healing wound on the left foot that had been developing over the past 10 weeks. Of note, the patient had already undergone an amputation of a portion of the big toe (right foot) for a non-healing diabetic ulcer. A review of the patient's medical history and an examination of the patient found that the patient: (1) had been diagnosed with diabetes mellitus 15 years previously and had been living with the condition since; (2) had no known drug allergies; (3) undergoes a daily regimen of 30 IU (70/30 Insulin-Novoline) in the A.M. and 10 IU (70/30 insulin) in the P.M.; (4) does not personally smoke or abuse alcohol; (5) (upon examination) had no other abnormalities in other systems, including the cardiovascular and respiratory systems; (6) (upon examination) had intact vital signs (Temp: 97.2 F, Pulse: 75/min; Blood Pressure: 110/70 mmHg; respiratory rate: 20/min.); and (7) (upon examination) had a blood sugar of about 160 mg.

Examination of the patient's left foot showed that the wound appeared to be infected. A greenish discharge was also noted at the wound site. The area around the wound was erythematous and there was noted tenderness on palpation. The size of the wound was recorded to be approximately 7 cm×2.5×2.0 cm. A wound swab also indicated the presence of *staphylococcus aureus*-methicillin sensitive. A treatment plan was established for the patient. Under the treatment plan, the patient received: 1) Insulin 70/30 (Novoline) 50 IU morning, 25 IU night; and 2) intravenously, Co-Amoxiclav 1.2 g+Gentamicin 80 mg+Metronidazole 400 mg in 100 ml N Saline/30 min. 8 hourly. for 24 hrs. After the injection of the intravenous antibiotics, the patient began taking oral antibiotics: 1) Co-Amoxiclav 625 mg (2 tablets) twice daily; 2) Ciprofloxacin 500 mg once daily for 2 weeks; and 3) Ibuprofen 600 mg for 5 days. Thereafter, the wound was cleaned with saline solution. To further promote wound healing, the patient was also started on Insulin R 25 IU 3 times daily. Further, a wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 5 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 10, the wound had healed completely.

Example 5

A 62-year old male patient was presented for a post-amputation, non-healing wound on the left foot that had been developing over the past 4 weeks. Of note, the patient had already undergone an amputation of a portion of the big toe (right foot) for a non-healing diabetic ulcer. A review of the patient's medical history and an examination of the patient found that the patient: (1) had been diagnosed with diabetes mellitus 8 years previously and had been living with the condition since; (2) had no known drug allergies; (3) undergoes a daily regimen of 30 IU (70/30 Insulin-Novoline) in the A.M. and 10 IU (70/30 insulin) in the P.M.; (4) does not personally smoke or abuse alcohol; (5) (upon examination) had no other abnormalities in other systems, including the cardiovascular and respiratory systems; (6) (upon examination) had intact vital signs (Temp: 100.00 F, Pulse: 100/min; Blood Pressure: 110/70 mmHg; Respiratory Rate: 20/min); and (7) (upon examination) had a blood sugar of about 200 mg.

Examination of the patient's left foot showed that the wound appeared to be infected. A greenish discharge was also noted at the wound site. The area around the wound was erythematous and there was noted tenderness on palpation. The size of the wound was recorded to be approximately 8 cm×4 cm×3 cm. A wound swab also indicated the presence of mixed flora. A treatment plan was established for the patient. Under the treatment plan, the patient received: 1) Insulin 70/30 (Novoline) 40 IU morning, 20 IU night; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) (twice daily); 2) Ciprofloxacin 500 mg once daily for 2 weeks; and 3) Ibuprofen 600 mg every 8 hours for 5 days. Thereafter, the wound was cleaned with saline solution. The patient recently started on Insulin R 25 IU 3 times daily over the past 10 weeks to control blood sugar so as to not inhibit wound healing. In addition, a wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 7 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 12, the wound had healed completely.

Example 6

A 64-year old female patient was presented for a post-amputation, non-healing wound that had been developing over the past week. Of note, the patient had already undergone an amputation of a portion of the below knee (right leg) for a non-healing diabetic ulcer. A review of the patient's medical history and an examination of the patient found that the patient: (1) had been diagnosed with diabetes mellitus 22 years previously and had been living with the condition since; (2) had no known drug allergies; (3) undergoes a daily regimen of 30 IU (70/30 Insulin-Novoline) in the A.M. and 10 IU (70/30 insulin) in the P.M.; (4) does not personally smoke or abuse alcohol; (5) (upon examination) had no other abnormalities in other systems, including the cardiovascular and respiratory systems; (6) (upon examination) had intact vital signs (Temp: 97.2 F, Pulse: 75/min; Blood Pressure: 110/70 mmHg; respiratory rate: 20/min.); and (7) (upon examination) had a blood sugar of about 160 mg.

Examination of the patient's right lower leg showed that the wound appeared to be infected. A greenish discharge was also noted at the wound site. The area around the wound was erythematous and there was noted tenderness on palpation. The size of the wound was recorded to be approximately 12 cm×5 cm×2 cm. Of note, stitches from the previous amputation of the right leg had broken in 3 places. A wound swab also indicated the presence of *staphylococcus aureus*-methicillin resistant. A treatment plan was established for the patient. Under the treatment plan, the patient received: 1) Insulin 70/30 (Novoline) 50 IU morning, 25 IU night; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) twice daily; 2) Ciprofloxacin 500 mg once daily for 2 weeks; and 3) Ibuprofen 600 mg (every 8 hours) for 5 days. Thereafter, the wound was cleaned with saline solution. The patient recently started on Insulin R 25 IU 3 times daily for the past 10 weeks to control blood sugar so as to not inhibit wound healing. A wound composition comprising a mixture of 300 mg powdered phenytoin (Dilantin®) and 500 mg of powdered Vitamin C was administered over the wound and the wound was dressed. The patient was advised to come back on daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 5 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 10, the wound had healed completely.

Example 7

A 69-year old male patient was presented for a laceration, located on the heal of the right foot. Of note, the patient had developed the present wound over at least the previous week. Previously also, the patient had been seen by a general surgeon for the present wound and advised to have an amputation of the right leg. A review of the patient's medical history and an examination of the patient found that the patient: (1) had been diagnosed with diabetes mellitus 10 years previously and had been living with the condition since; (2) had no known drug allergies; (3) undergoes a daily regimen of 30 IU (70/30 Insulin-Novoline) in the A.M. and 10 IU (70/30 insulin) in the P.M.; (4) does not personally smoke or abuse alcohol; (5) (upon examination) had no other abnormalities in other systems, including the cardiovascular and respiratory systems; (6) She had intact vital signs (Temp: 99.5° F., Pulse: 110/min; Blood Pressure: 110/70 mmHg; respiratory rate: 20/min.); and (7) (upon examination) had a blood sugar of about 160 mg.

Examination of the patient's right foot showed that the wound appeared to be infected. A greenish discharge was also noted at the wound site. The area around the wound was erythematous and there was noted tenderness on palpation. The size of the wound was recorded to be approximately 5 cm×2 cm×3 cm. A wound swab also indicated the presence of *staphylococcus aureus*-methicillin sensitive. A treatment plan was established for the patient. Under the treatment plan, the patient received: 1) Insulin 70/30 (Novoline) 30 IU morning, 10 IU night; and 2) intravenously, Co-Amoxiclav 1.2 g+Gentamicin 80 mg+Metronidazole 400 mg in 100 ml N Saline/30 min. every 8 hours. After the injection of the intravenous antibiotics, the patient began taking oral antibiotics: 1) Co-Amoxiclav 625 mg (2 tablets) twice daily; 2) Ciprofloxacin 500 mg once daily for 2 weeks; and 3) Ibuprofen 600 mg (every 8 hours) for 5 days. Thereafter, the wound was cleaned with saline solution. A wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 9 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 10, approximately 90% of the wound had healed. At week 11, the wound had completely healed and the recommendation of amputation was not carried out.

Example 8

A 68-year old male patient was presented for a non-healing diabetic ulcer on the patient's lower right leg that had developed over at least the past week. Of note, a review of the patient's medical history and an examination of the patient found that the patient: (1) had been diagnosed with diabetes mellitus 15 years previously and had been living with the condition since; (2) had no known drug allergies; (3) does not personally smoke or abuse alcohol; (4) undergoes a daily regimen of 30 IU (70/30 Insulin-Novoline) in the A.M. and 10 IU (70/30 insulin) in the P.M.; (5) (upon examination) had no other abnormalities in other systems, including the cardiovascular and respiratory systems; (6) (upon examination) had intact vital signs (Temp: 97.2 F, Pulse: 75/min; Blood Pressure: 110/70 mmHg; respiratory rate: 20/min); and (7) (upon examination) had a blood sugar of about 186 mg.

Examination of the patient's right lower leg showed that the wound appeared to be infected. A greenish discharge was also noted at the wound site. The area around the wound was erythematous and there was noted tenderness on palpation. The size of the wound was recorded to be approximately 5 cm×2 cm×2 cm. A wound swab also indicated the presence of *staphylococcus aureus*-methicillin resistant. A treatment plan was established for the patient. Under the treatment plan, the patient received: 1) Insulin 70/30 (Novoline) 50 IU morning, 25 IU night; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) twice daily; 2) Ciprofloxacin 500 mg once daily for 2 weeks; and 3) Ibuprofen 600 mg every 8 hours for 5 days. Thereafter, the wound was cleaned with saline solution. The patient was also started on Insulin R 25 IU 3 times daily to control blood sugar so as to not inhibit wound healing. Further, a wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 8 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 5 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 70% of the wound had healed and a substantial amount of granulation tissue (approximately 40%) had formed. At week 9, approximately 80% of the wound had healed. At week 10, the wound had healed completely.

Example 9

A 62-year old male patient was presented for a post-amputation, non-healing wound located on the patient's right leg that had developed over the past week. Of note, the patient had already undergone an amputation of a portion of the leg (right leg) for a non-healing diabetic ulcer. A review of the patient's medical history and an examination of the patient found that the patient: (1) had been diagnosed with diabetes mellitus 22 years previously and had been living with the condition since; (2) had no known drug allergies; (3) does not personally smoke or abuse alcohol; (4) undergoes a daily regimen of 30 IU (70/30 Insulin-Novoline) in the A.M. and 10 IU (70/30 insulin) in the P.M.; (5) (upon examination) had no other abnormalities in other systems, including the cardiovascular and respiratory systems; (6) (upon examination) had intact vital signs (Temp: 97.2 F, Pulse: 75/min; Blood Pressure: 110/70 mmHg; respiratory rate: 20/min); and (7) (upon examination) had a blood sugar of about 160 mg.

Examination of the patient's right lower leg showed that the wound appeared to be infected. A greenish discharge was also noted at the wound site. The area around the wound was erythematous and there was noted tenderness on palpation. The size of the wound was recorded to be approximately 12 cm×5 cm×2 cm. Stitches from the previous amputations had broken in three different places. A wound swab also indicated the presence of *staphylococcus aureus*-methicillin resistant. A treatment plan was established for the patient. Under the treatment plan, the patient received: 1) Insulin 70/30 (Novoline) 50 IU morning, 25 IU night; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) (twice daily); 2) Ciprofloxacin 500 mg once daily for 2 weeks; and 3) Ibuprofen 600 mg every 8 hours for 5 days. Thereafter, the wound was cleaned with saline solution. The patient was also started on Insulin R 25 IU 3 times daily to control blood sugar so as to not inhibit wound healing. A wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 5 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 10, the wound had healed completely.

Example 10

An 80-year old female patient was presented for a non-healing ulcer on the right foot between the 3$^{rd}$ and 4$^{th}$ toe that has been developing for at least the last 12 weeks. The patient: (1) had been diagnosed with diabetes mellitus 25 years previously and had been living with the condition since; (2) had no known drug allergies; (3) does not personally smoke or abuse alcohol; (4) undergoes a daily regimen of 30 IU (70/30 Insulin-Novoline) in the A.M. and 10 IU (70/30 insulin) in the P.M.; (5) (upon examination) had no other abnormalities in other systems, including the cardiovascular and respiratory systems; (6) (upon examination) had intact vital signs (Temp: 100.2 F; Pulse: 110/min; Blood Pressure: 110/70 mmHg; respiratory rate: 20/min); and (7) (upon examination) had a blood sugar of about 210 mg.

Examination of the patient's right foot showed that the wound appeared to be infected. A discharge was also noted at the wound site. The area around the wound was erythematous and there was noted tenderness on palpation. The size of the wound was recorded to be approximately 5 cm×2 cm×2 cm. A wound swab also indicated the presence of *staphylococcus aureus*-methicillin sensitive. A treatment plan was established for the patient. Under the treatment plan, the patient received: 1) Insulin 70/30 (Novoline) 50 IU morning, 25 IU night; 2) I.V. Agumentin 1.2 g+I.V. Gentamycine 80 mg+I.V. Flagil 400 mg in 100 mg N saline over 30 minutes every 8 hours; 3) Co-Amoxiclav 625 mg (2 tablets) twice daily; 3) Ciprofloxacin 500 mg once daily for 2 weeks; and 4) Ibuprofen 600 mg every 8 hours for 5 days. Thereafter, the wound was cleaned with saline solution. A wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 7 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 10, approximately 90% of the wound had healed. Within another two weeks, the wound had completely healed.

Example 11

A 62-year old male patient was presented for a post-amputation, non-healing wound located on the right lower leg that had been developing over at least the past week. Of note, the patient had already undergone an amputation of a portion of the leg below the knee (right leg) for a non-healing diabetic ulcer. A review of the patient's medical history and an examination of the patient found that the patient: (1) had been diagnosed with diabetes mellitus 22 years previously and had been living with the condition since; (2) had no known drug allergies; (3) does not personally smoke or abuse alcohol; (4) undergoes a daily regimen of 30 IU (70/30 Insulin-Novoline) in the A.M. and 10 IU (70/30 insulin) in the P.M.; (5) (upon examination) had no other abnormalities in other systems, including the cardiovascular and respiratory systems; (6) (upon examination) had intact vital signs (Temp: 97.2° F.; Pulse: 75/min; Blood Pressure: 110/70 mmHg; respiratory rate: 20/min.); and (7) (upon examination) had a blood sugar of about 160 mg.

Examination of the patient's right lower leg showed that the wound appeared to be infected. A greenish discharge was also noted at the wound site. The area around the wound was erythematous and there was noted tenderness on palpation. The size of the wound was recorded to be approximately 12 cm×5 cm×2 cm. Stitches from the previous amputation had broken in 3 places. A wound swab also indicated the presence of *staphylococcus aureus*-methicillin resistant. A treatment plan was established for the patient. Under the treatment plan, the patient received: 1) Insulin 70/30 (Novoline) 50 IU morning, 25 IU night; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) twice daily; 2) Ciprofloxacin 500 mg once daily for 2 weeks; and 3) Ibuprofen 600 mg every 8 hours for 5 days. Thereafter, the wound was cleaned with saline solution. The patient was also started on Insulin R 25 IU 3 times daily to control blood sugar so as to not inhibit wound healing. A wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 5 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 80% of the wound had healed. At week 10, the wound had healed completely.

Example 12

A 55-year old male patient was presented for an ulcer on the medial aspect of the left lower leg 7.5 cm from the left knee joint that had been developing for at least the past 6 months. Of note, examination of the patient found that the patient: (1) had been diagnosed with diabetes mellitus six month previously and had been living with the condition since; (2) had no known drug allergies; (3) does not personally smoke or abuse alcohol; (4) undergoes a daily regimen of 30 IU (70/30 Insulin-Novoline) in the A.M. and 10 IU (70/30 insulin) in the P.M.; (5) (upon examination) had no other abnormalities in other systems, including the cardiovascular and respiratory systems; (6) (upon examination) had intact vital signs (Temp: 97.2 F, Pulse: 75/min; Blood Pressure: 160/95 mmHg; Respiratory Rate: 20/min.); and (6) (upon examination) had a blood sugar of about 160 mg.

Examination of the patient's left leg showed that the wound appeared to be infected. A greenish discharge was also noted at the wound site. The area around the wound was erythematous and there was noted tenderness on palpation. The size of the wound was recorded to be approximately 4 cm×2.5 cm×2 cm. A wound swab also indicated the presence of *staphylococcus aureus-streptococcus* methicillin resistant. A treatment plan was established for the patient. Under the treatment plan, the patient received: 1) Tab Amaryl 4 mg three times a day+Tab Glucophage 500 mg 3 times a day; (2) Tab Diovan 80 mg+Tab Lasix 40 mg once daily in A.M+Tab ciprifloxin 500 mg once daily for 2 weeks; and 3) Ibuprofen 600 mg every 8 hours for 5 days. Thereafter, the wound was cleaned with saline solution. The patient was also started on Insulin R 25 IU 3 times daily to control blood sugar so as to not inhibit wound healing. Further, a wound composition comprising a mixture of 300 mg powdered phenytoin (Dilantin®) and 500 mg of powdered Vitamin C was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after the 9 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 60% of the wound had healed and a substantial amount of granulation tissue (approximately 40%) had formed. At week 9, approximately 70% of the wound had healed. Thereafter, the patient had stop coming to the office. After 3 weeks, the patient returned, but the wound was unhealthy. The importance of weekly visits was stressed. After application of the wound composition 2×/week for the next two weeks, the wound again healed to about 70%. After an additional 13 weeks, the wound had healed completely.

The following five (5) case studies included the use of Dilantin alone

Example 13

A 80-year old male patient was presented for a non-healing wound located on the right foot of the patient that had been developing for at least the past 14 weeks. A review of the patient's medical history and an examination of the patient found that the patient: (1) had been diagnosed with diabetes mellitus 20 years previously and had been living with the condition since; (2) had no known drug allergies; (3) does not personally smoke or abuse alcohol; (4) undergoes a daily regimen of 30 IU (70/30 Insulin-Novoline) in the A.M. and 10 IU (70/30 insulin) in the P.M.; (5) (upon examination) had no other abnormalities in other systems, including the cardiovascular and respiratory systems; (6) (upon examination) had intact vital signs (Temp: 96.2 F, Pulse: 75/min; Blood Pressure: 170/95 mmHg; Respiratory Rate: 20/min.; and (7) (upon examination) had a blood sugar of about 180 mg.

Examination of the patient's right foot showed that the wound appeared to be infected. A greenish discharge was also noted at the wound site. The area around the wound was erythematous and there was noted tenderness on palpation. The size of the wound was recorded to be approximately 6 cm×3 cm×3 cm. A wound swab also indicated the presence of *staphylococcus aureus*-methicillin resistant. A treatment plan was established for the patient. Under the treatment plan, the patient received: 1) Insulin 70/30 (Novoline) 40 IU morning, 20 IU night; and 2) intravenously, Co-Amoxiclav 1.2 g+Gentamicin 80 mg+Metronidazole 400 mg in 100 ml N Saline/30 min. every 8 hours. After the injection of the intravenous antibiotics, the patient began taking oral antibiotics: 1) Co-Amoxiclav 625 mg (2 tablets) twice daily 2) Ciprofloxacin 500 mg once daily for 2 weeks; and 3) Ibuprofen 600 mg every 8 hours; and (4) Co-diovan tablets (valsartan and hydrochlorothiazide) 80 mg/12.5 mg daily. Thereafter, the wound was cleaned with saline solution. A wound composition comprising 300 mg powdered phenytoin (Dilantin®) was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 7 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 35% of the wound had healed and granulation tissue (approximately 20%) had formed. At week 9, approximately 40% of the wound had healed. At week 10, approximately 60% of the wound had healed. The wound took nearly 20 weeks to heal completely. Thereafter, the wound returned in substantially the same location. Thereafter, the patient saw a surgeon who advised him of the need to amputate the right leg below the knee. No further treatment was prescribed to the patient.

Example 14

A 67-year old male patient was presented for non-healing wound located on the left foot that had been developing for at least the past 3 weeks. A review of the patient's medical history and an examination of the patient found that the patient: (1) had been diagnosed with diabetes mellitus 35 years previously and had been living with the condition since; (2) had no known drug allergies; (3) does not personally smoke or abuse alcohol; (4) undergoes a daily regimen of 30 IU (70/30 Insulin-Novoline) in the A.M. and 10 IU (70/30 insulin) in the P.M.; (5) (upon examination) had no other abnormalities in other systems, including the cardiovascular and respiratory systems; (6) (upon examination) had intact vital signs (Temp: 97.2 F, Pulse: 75/min; Blood Pressure: 110/70 mmHg; Respiratory Rate: 16/min.); and (7) (upon examination) had a blood sugar of about 190 mg.

Examination of the patient's left foot showed that the wound appeared to be infected. A greenish discharge was also noted at the wound site. The area around the wound was erythematous and there was noted tenderness on palpation. The size of the wound was recorded to be approximately 5 cm×2 cm×3 cm. A wound swab also indicated the presence of staphylococcus aureus-methicillin resistant. A treatment plan was established for the patient. Under the treatment plan, the patient received: 1) Insulin 70/30 (Novoline) 30 I.U. morning, 15 IU night; and 2) intravenously, Co-Amoxiclav 1.2 g+Gentamicin 60 mg+Metronidazole 400 mg in 100 ml N Saline/30 min. every 8 hours. After the injection of the intravenous antibiotics, the patient began taking oral antibiotics: 1) Co-Amoxiclav 625 mg (2 tablets) twice daily; 2) Ciprofloxacin 500 mg once daily for 2 weeks; and 3) Ibuprofen 600 mg every 8 hours for 5 days. Thereafter, the wound was cleaned with saline solution. A wound composition comprising 300 mg powdered phenytoin (Dilantin®) was administered over the wound and the wound was dressed. The patient was advised to come back on a daily basis for dressing of the wound and reapplication of the wound composition.

The patient returned for 9 consecutive visits over the next 9 days. Thereafter, the patient began weekly visits. With each visit, the wound was cleaned with saline solution and the powdered wound composition was applied topically to the wound, and redressed. In each visit, the wounds were noted to be generally healthy. At week 1 (after 7 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well, but was very slow healing. At week 8, approximately 25 of the wound had healed and granulation tissue (approximately 20%) had formed. At week 9, approximately 40% of the wound had healed. At week 10, approximately wound was approximately 60% healed and the wound took nearly 27 weeks to heal completely. Unfortunately, after 9 months, the wound returned in approximately the same location. The patient then went to see a surgeon who advised him of the need to amputate the left leg below the knee.

Example 15

A 54-year old male patient was presented for non-healing wound located on the left foot that had been developing over at least the past 6 weeks. A review of the patient's medical history and an examination of the patient found that the patient: (1) had been diagnosed with hypertension 15 years previously and peripheral arterial disease, and had been living with these conditions since; (2) had no known drug allergies; (3) does not personally smoke or abuse alcohol; and (4) (upon examination) had intact vital signs (Temp: 97.2° F.; Pulse: 75/min; Blood Pressure: 200/100 mmHg; Respiratory Rate: 20/min); and (5) (upon examination) had a blood sugar of about 98 mg.

Examination of the patient's left foot showed that the wound appeared to be infected. A greenish discharge was also noted at the wound site. The area around the wound was erythematous and there was noted tenderness on palpation. The size of the wound was recorded to be approximately 9 cm×4 cm×3 cm. A wound swab also indicated the presence of staphylococcus aureus-methicillin resistant. A treatment plan was established for the patient. Under the treatment plan, the patient received: 1) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) (twice daily); 2) Ciprofloxacin 500 mg once daily for 2 weeks; and 3) Ibuprofen 600 mg (every 8 hours). Thereafter, the wound was cleaned with saline solution. A wound composition comprising 300 mg powdered phenytoin (Dilantin®) was administered over the wound and the wound was dressed. The patient was advised to return on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 7 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 25% of the wound had healed and granulation tissue (approximately 20%) was formed. At week 9, approximately 40% of the wound had healed. At week 10, the wound was approximately 60% healed. The wound took nearly 22 weeks to heal completely. Nevertheless, one year thereafter, the wound returned in substantially the same location. The patient then went to see a surgeon who advised him of the need to amputate the left leg below the knee.

Example 16

A 80-year old female patient was presented for non-healing wound located on the right foot that had been developing for at least the previous 3 weeks. A review of the patient's medical history and an examination of the patient found that the patient: (1) had been diagnosed with diabetes mellitus 30 years previously and had been living with the condition since; (2) had no known drug allergies; (3) does not personally smoke or abuse alcohol; (4) (upon examination) had no other abnormalities in other systems, including the cardiovascular and respiratory systems; (5) (upon examination) had intact vital signs (Temp: 97.2° F., Pulse: 75/min; Blood Pressure: 110/70 mmHg; Respiratory Rate 20/min); and (6) (upon examination) had a blood sugar of about 195 mg.

Examination of the patient's right foot showed that the wound appeared to be infected. A greenish discharge was also noted at the wound site. The area around the wound was erythematous and there was noted tenderness on palpation. The size of the wound was recorded to be approximately 4.5 cm×2 cm×3 cm. A wound swab also indicated the presence of *staphylococcus aureus*-methicillin resistant. A treatment plan was established for the patient. Under the treatment plan, the patient received: 1) Insulin 70/30 (Novoline) 30 IU morning, 15 IU in the evening; and 2) intravenously, Co-Amoxiclav 1.2 g+Gentamicin 80 mg+Metronidazole 400 mg in 100 ml N Saline/30 min. every 8 hours. After the injection of the intravenous antibiotics, the patient began taking oral antibiotics: 1) Co-Amoxiclav 625 mg (2 tablets) twice daily; 2) Ciprofloxacin 500 mg once daily for 2 weeks; and 3) Ibuprofen 600 mg every 8 hours. Thereafter, the wound was cleaned with saline solution. A wound composition comprising 300 mg powdered phenytoin (Dilantin®) was administered over the wound and the wound was dressed. The patient was advised to come back on a daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 7 consecutive visits), there were signs of new skin formation (wound healing by secondary intention). At weeks 3-5 the wound continued to appear generally healthy and the patient was advised to maintain strict diabetic control. At weeks 5-7, it was noted that the wound was beginning to heal very well. At week 8, approximately 25% of the wound had healed and a granulation tissue (approximately 20% had formed. At week 9, approximately 40% of the wound had healed. At week 13, approximately 60% of the wound had healed. The wound took nearly 25 weeks to heal completely. Nevertheless, thereafter, the wound returned in substantially the same location. The patient then went to see a surgeon who advised her of the need to amputate the right leg below the knee. No further treatment was given and the patient went for a second opinion.

Example 17

A 60-year old male patient was presented for non-healing wound located the left foot that had been developing over at least the past 3 weeks. A review of the patient's medical history and an examination of the patient found that the patient: (1) had been diagnosed with diabetes mellitus 25 years previously and had been living with the condition since; (2) had no known drug allergies; (3) does not personally smoke or abuse alcohol; (4) (upon examination) had no other abnormalities in other systems, including the cardiovascular and respiratory systems; (5) (upon examination) had intact vital signs (Temp: 97.2 F, Pulse: 75/min; Blood Pressure: 110/70 mmHg; (Respiratory Rate: 20/min.); and (6) (upon examination) had a blood sugar of about 240 mg.

Examination of the patient's left foot showed that the wound appeared to be infected. A greenish discharge was also noted at the wound site. The area around the wound was erythematous and there was noted tenderness on palpation. The size of the wound was recorded to be approximately 9 cm×4 cm×3 cm. A wound swab also indicated the presence of *staphylococcus aureus*-methicillin resistant. A treatment plan was established for the patient. Under the treatment plan, the patient received: 1) Insulin 70/30 (Novoline) 50 IU morning, 25 IU night; and 2) intravenously, Co-Amoxiclav 1.2 g+Gentamicin 80 mg+Metronidazole 400 mg in 100 ml N Saline/30 min. (every 8 hours). After the injection of the intravenous antibiotics, the patient began taking oral antibiotics: 1) Co-Amoxiclav 625 mg (2 tablets) q12; 2) Ciprofloxacin 500 mg once daily for 2 weeks; and 3) Ibuprofen 600 mg 8 hourly for 5 days. Thereafter, the wound was cleaned with saline solution. A wound composition comprising 300 mg powdered phenytoin (Dilantin®) was administered over the wound and the wound was dressed. The patient was advised to come back on daily basis for dressing of the wound and reapplication of the wound composition.

The patient returned for 9 consecutive visits over the next nine days. Thereafter, the patient began weekly visits. With each visit, the wound was cleaned with saline solution and the powdered wound composition was applied topically to the wound, and redressed. In each visit, the wounds were noted to be generally healthy. At week 1 (after 7 consecutive visits), there were signs of new skin formation (wound healing by secondary intention). At weeks 2-4, the wound continued to appear generally healthy and the patient was advised to maintain strict diabetic control. At weeks 5-7, it was noted that the wound was beginning to heal very well. At week 8, approximately 25% of the wound had healed and granulation tissue (approximately 20%) had formed. At week 9, approximately 40% of the wound had healed. At week 10, approximately 60% of the wound had healed and the wound took nearly 22 weeks to heal completely. Nevertheless, thereafter, the wound returned in substantially the same location. The patient then went to see a surgeon who advised him of the need to amputate the right leg below the knee. No further treatment was prescribed to the patient.

The teachings of the references cited throughout the specification are incorporated herein in their entirety by this reference to the extent they are not inconsistent with the teachings herein. It should be understood that the examples and the embodiments described herein are for illustrative purposes only and that various modifications or changes in light thereof will be suggested to persons skilled in the art and are to be included within the spirit and purview of this application.

The invention claimed is:

1. A method for treating a diabetic ulcer comprising administering to a patient in need thereof a wound composition consisting essentially of an effective amount of phenytoin and an effective amount of vitamin C, wherein the composition is provided in a form comprising a powder, ointment, lotion, cream, and/or gel.

2. The method of claim 1, wherein the ratio of phenytoin to vitamin C is from about 1:10 to about 1:1.

3. The method of claim 2, wherein the ratio of phenytoin to vitamin C is about 3:5.

4. The method of claim 1, wherein the wound composition is administered via topical administration.

5. The method of claim 1, wherein the wound composition is administered via parenteral administration.

6. The method of claim 1, wherein the wound composition is administered to the patient at least once daily for at least seven days, and thereafter at least once weekly for at least eight weeks.

7. A method for treating a diabetic ulcer comprising administering to a patient in need thereof a pharmaceutical composition consisting essentially of an effective amount of phenytoin, an effective amount of vitamin C, and at least one pharmaceutical acceptable excipient, wherein the pharmaceutical composition is provided in a form comprising a powder, ointment, lotion, cream, and/or gel.

\* \* \* \* \*